United States Patent
Mouri et al.

[11] Patent Number: 6,074,378
[45] Date of Patent: Jun. 13, 2000

[54] SELF-RETAINING CATHETER AND INSERTING APPARATUS THEREOF

[75] Inventors: Makoto Mouri, Tokyo; Nobuhiko Tanaka; Yukihisa Kurebayashi, both of Yokohama, all of Japan

[73] Assignee: Piolax Inc., Kanagawa-ken, Japan

[21] Appl. No.: 09/093,373

[22] Filed: Jun. 8, 1998

[51] Int. Cl.[7] .................................................. A61M 25/00
[52] U.S. Cl. ......................... 604/523; 604/530; 604/508; 604/264
[58] Field of Search ..................... 604/523, 524, 604/525, 526, 532, 530, 264, 500, 507, 508

[56] References Cited

U.S. PATENT DOCUMENTS

| | | | |
|---|---|---|---|
| 4,681,570 | 7/1987 | Dalton | 604/523 |
| 5,282,860 | 2/1994 | Matsuno et al. | 633/12 |
| 5,554,114 | 9/1996 | Wallace . | |
| 5,603,694 | 2/1997 | Brown et al. | 604/523 X |
| 5,709,874 | 1/1998 | Harker . | |
| 5,730,741 | 3/1998 | Horzewski . | |
| 5,873,865 | 2/1999 | Horzewski et al. | 604/523 |

FOREIGN PATENT DOCUMENTS

| | | |
|---|---|---|
| 0244818 | 11/1987 | European Pat. Off. . |
| 0513991 | 11/1992 | European Pat. Off. . |
| 2661603 | 11/1991 | France . |
| 5-86355 | 11/1993 | Japan . |

*Primary Examiner*—John D. Yasko
*Attorney, Agent, or Firm*—Ladas & Parry

[57] ABSTRACT

In a self-retaining catheter in which a leading end of the catheter can be fixed to an inner wall of a tubular organ such as a blood vessel, a wire with higher stiffness than a catheter body and in a winding shape greater than an outside diameter of the catheter body is mounted inside a leading end of the catheter body or in a projecting state from the leading end of the catheter body. An aperture of a slit shape is formed in a peripheral wall of the catheter body, in order to allow a medical fluid to flow out therethrough. A self-retaining catheter inserting apparatus includes the above-stated self-retaining catheter, a core wire arranged to be inserted into and withdrawn from the self-retaining catheter, a master catheter through which the self-retaining catheter can pass, and a sheath necessary for the master catheter to be inserted into a tubular organ, and preferably, the apparatus further includes a medical fluid injection port.

14 Claims, 8 Drawing Sheets

SELF-RETAINING CATHETER AND INSERTING APPARATUS THEREOF

BACKGROUND OF THE INVENTION

1. Field of the Invention

The present invention relates to a self-retaining catheter that is arranged to be retained in a blood vessel or the like of a patient and to permit a medical fluid, for example such as a carcinostatic, to be injected on a periodic basis, and an inserting apparatus thereof.

2. Related Background Art

For administration of such a medical fluid as a carcinostatic, for example, the medical fluid was administered into a blood vessel conventionally by use of an injection syringe or a drip. In that case, the medical fluid circulated through blood vessels in the body, and thus there was the fear of damaging the normal cells in addition to cancerous cells.

Under such circumstances, attempts have been made to achieve such techniques as to percutaneously insert a catheter into a blood vessel, locate the leading end of this catheter at an arterial inlet to an organ affected by cancer, and directly inject the medical fluid into the organ affected by cancer, thereby accomplishing a prominent carcinostatic effect even with a small dose of the medical fluid.

In this case, after the catheter was set so that the leading end thereof was located at the arterial inlet to the target organ, injection of the medical fluid was carried out while the base side of the catheter was fixed to the patient's body so as to prevent the leading end of the catheter from shifting from the position.

In order to prevent the medical fluid from flowing into arteries branched to the other normal organs, embolization coils or the like were inserted into inlets of the arteries branched to the other normal organs so as to temporarily obstruct the blood flow, so that the medical fluid could flow into only the organ affected by cancer.

On the other hand, there are conventionally known catheters having the structure capable of retaining themselves not only in the blood vessels, but also in tubular organs of the human body, and an example of such catheters is the one described in Japanese Patent Application Laid-open No. 5-192389, in which the catheter is comprised of an outside tube, an inside tube, and a reinforcement interposed between them, and in which a flap projecting to engage an inner wall of a tubular organ of the human body is mounted on the periphery of the leading end of the outside tube.

Another known example is the one described in Japanese Utility Model Application Laid-open No. 5-86355, in which a plurality of fins are arranged at intervals on the periphery of the leading end or an intermediate section of the catheter so as to act as a cushion, a seal, a stopper, and a protector.

In treatments by the conventional method for locating the leading end of the catheter at the inlet of the artery to the affected organ as a target and directly feeding the medical fluid into the target organ, there sometimes occurred, however, accidents that the position of the leading end of the catheter shifted because of a body motion, such as tossing, of the patient on the occasion of injection of the medical fluid, so as to cause the medical fluid to flow into the other organs than the target organ, though the base side of the catheter was fixed to the patient's body.

Further, it was not easy to apply the self-retaining catheter described in Japanese Patent Application Laid-open No. 5-192389 to a tubular organ comprised of a narrow and thin wall, such as a blood vessel, because the flap projecting from the periphery of the leading end of the catheter tended to damage the internal wall of the tubular organ.

With the self-retaining catheter described in Japanese Utility Model Application Laid-open No. 5-86355, the fins also tended to damage the internal wall of the tubular organ and in applications to the blood vessels or the like, it was difficult to retain the catheter over the long term, because the fins obstructed the blood flow.

SUMMARY OF THE INVENTION

An object of the present invention is to provide a self-retaining catheter whose leading end can be fixed to an inner wall of a tubular organ such as a blood vessel, that causes little damage to the inner wall of the tubular organ during insertion and during withdrawal, and that causes little obstruction against the blood flow or the like in the self-retaining state, and also to provide an inserting apparatus of the self-retaining catheter.

In order to accomplish the above object, a self-retaining catheter according to the present invention comprises a tubular catheter body, and an elastic wire of a winding shape buried in one end portion of the catheter body, wherein the end portion of the catheter body with the wire inside is in a winding state.

In this structure, when the leading end of the self-retaining catheter is guided to a target portion of a tubular organ such as a blood vessel to be retained there, the catheter body starts to go back into the winding state because of the wire buried inside the leading end of the catheter body, whereby the catheter body is fixed while being elastically urged against the inner wall of the tubular organ. In this case there occurs little damage to the inner wall of the tubular organ, because the catheter body is fixed while being urged against the inner wall of the tubular organ by the winding shape of the catheter body, different from the structures wherein the flap or fins projecting from the catheter engage the inner wall of the tubular organ. Since the catheter body is in the winding state, a clearance is created between the catheter body and the inner wall of the tubular organ, so that the catheter does not obstruct the blood flow or the like.

When the self-retaining catheter is withdrawn, a master catheter is inserted along the periphery of the self-retaining catheter. Then the self-retaining catheter is pulled to the base side relative to the master catheter, so as to retract the self-retaining catheter into the master catheter while stretching the leading end of the self-retaining catheter. This simple operation permits the self-retaining catheter to be withdrawn, and thus the withdrawal (evulsion) of the self-retaining catheter can be performed readily.

Another embodiment of the self-retaining catheter according to the present invention comprises a tubular catheter body, and an elastic wire of a winding shape greater than an outside diameter of the catheter body, wherein said wire is connected to one end of the catheter body so as to project outwardly from the catheter body.

In this structure, when the leading end of the self-retaining catheter is guided to a target portion of the tubular organ such as the blood vessel to be retained there, the wire connected to the leading end of the catheter body starts to go back into the winding state, so that the wire becomes fixed while being elastically urged against the inner wall of the tubular organ. Therefore, the self-retaining catheter causes little damage to the inner wall of the tubular organ and does not obstruct the blood flow or the like, from the same reasons as described above.

The catheter can be constructed in such a structure that the catheter body linearly extends from a position in a periphery of the winding shape of the wire.

In this structure, when the leading end of the catheter body is fixed inside the tubular organ such as the blood vessel, the base side of the catheter body extends from the position in the periphery of the winding shape of the leading end and along the inner wall of the tubular organ. Therefore, this structure causes little obstruction to flow of the body fluid such as the blood flow and can prevent occurrence of a thrombus or the like.

The catheter can be constructed in such a structure that an aperture for outflow of a medical fluid is formed in a peripheral wall of the catheter body near the end where the wire is mounted, the aperture is formed in a slit shape, the aperture is opened when a pressure of the fluid inside is applied thereto, and the aperture is closed when the pressure of the fluid inside is not applied thereto.

In this structure, after the medical fluid flows in the axial direction inside the catheter body, the medical fluid changes its direction so as to flow sideways out of the aperture formed in the peripheral wall. This restrains the medical fluid from hitting the inner wall of the tubular organ such as the blood vessel with strong force and in turn, it can avoid obstruction of a flow passage or the like due to the damage to the inner wall of the blood vessel or the like. Since the aperture is of the slit shape and is opened only when the pressure of the fluid inside is applied thereto, the body fluid such as the blood can be prevented from flowing back through the catheter during the periods in which the medical fluid is not injected.

In the conventional methods, the medical fluid introduced into the catheter advanced along the axis of the catheter and flowed straight out of the leading end thereof. Thus the conventional methods had the problem that the medical fluid hit the inner wall of the blood vessel, the blood vessel absorbed the medical fluid, it damaged the inner wall of the blood vessel, and it was likely to cause obstruction in the blood vessel. In the present invention, where the aperture for outflow of the medical fluid is formed in the peripheral wall of the catheter body, the medical fluid is, however, prevented from directly hitting the inner wall of the blood vessel or the like with strong force, which can prevent the obstruction due to the damage to the inner wall of the blood vessel or the like.

The self-retaining catheter can be constructed in such a structure that an aperture for outflow of the medical fluid is formed in a peripheral wall of the catheter body near the end where the wire is mounted and that the aperture is formed as being directed toward the center of the winding shape of the wire, in the peripheral wall of the catheter body.

In this structure, where the aperture of the catheter body is directed toward the center of the winding shape of the wire, i.e., inwardly inside the tubular organ, the medical fluid is prevented from strongly hitting the inner wall of the tubular organ, because the aperture is directed toward the center of the tubular organ. Thus there occurs little damage to the inner wall.

The self-retaining catheter can be constructed in such a structure that a contrast chip is mounted near the aperture of the catheter body.

In this structure, where the contrast chip is mounted near the aperture of the catheter body, a position of the medical fluid injection aperture can be detected with accuracy, and the medical treatment can be carried out more precisely.

A self-retaining catheter inserting apparatus according to the present invention comprises the self-retaining catheter according to the present invention, a core wire arranged to be detachably inserted into the self-retaining catheter, and a master catheter having an inside diameter that permits insertion of the self-retaining catheter.

In this structure, the self-retaining catheter can be guided to a predetermined portion in a tubular organ through the master catheter, and the self-retaining catheter can be fixed in the tubular organ by restoring force of the wire when the leading end of the self-retaining catheter is made to project out of the master catheter. In this case, the insertion operation of the self-retaining catheter can be facilitated with increase in the stiffness thereof by inserting the core wire into the self-retaining catheter.

Another embodiment of the self-retaining catheter inserting apparatus according to the present invention comprises the self-retaining catheter according to the present invention, a core wire arranged to be detachably inserted into this self-retaining catheter, a master catheter having an inside diameter that permits insertion of the self-retaining catheter, and a sheath for percutaneous insertion of the master catheter into a blood vessel.

In this structure, the sheath is first percutaneously inserted into the blood vessel, the master catheter is then inserted through this sheath, the leading end of this master catheter is guided to a desired portion in the blood vessel, and the self-retaining catheter is inserted through this master catheter. Therefore, the insertion operation of the self-retaining catheter into the blood vessel can be performed surely and readily.

A further embodiment of the self-retaining catheter inserting apparatus according to the present invention comprises the self-retaining catheter according to the present invention, a core wire arranged to be detachably inserted into the self-retaining catheter, a master catheter having an inside diameter that permits insertion of the self-retaining catheter, a sheath for percutaneous insertion of the master catheter into a blood vessel, and a medical fluid injection port to be embedded in the body while being connected to a base end of the self-retaining catheter.

In this structure, the sheath is first percutaneously inserted into the blood vessel, the master catheter is then inserted through this sheath, and the leading end of this master catheter is guided to a desired portion in the blood vessel. Thereafter the self-retaining catheter is inserted through the master catheter, and the leading end of the self-retaining catheter is made to project out of the master catheter to be fixed to the inner wall of the blood vessel. Then the master catheter is drawn out, the medical fluid injection port is connected to the base end of the self-retaining catheter, and this medical fluid injection port is embedded under the skin. By this structure, an injection needle can be stuck into the medical fluid injection port when necessary and the medical fluid can be injected readily into the affected region of the target, which extremely reduces the load on the patient.

When the self-retaining catheter is withdrawn, the master catheter is inserted along the periphery of the self-retaining catheter. Then the self-retaining catheter is pulled to the base side relative to the master catheter, so as to retract the self-retaining catheter into the master catheter while stretching the leading end of the self-retaining catheter. This simple operation permits the self-retaining catheter to be withdrawn, and thus the withdrawal (evulsion) of the self-retaining catheter can be performed readily.

DETAILED DESCRIPTION OF THE PREFERRED EMBODIMENTS

Figure 1:
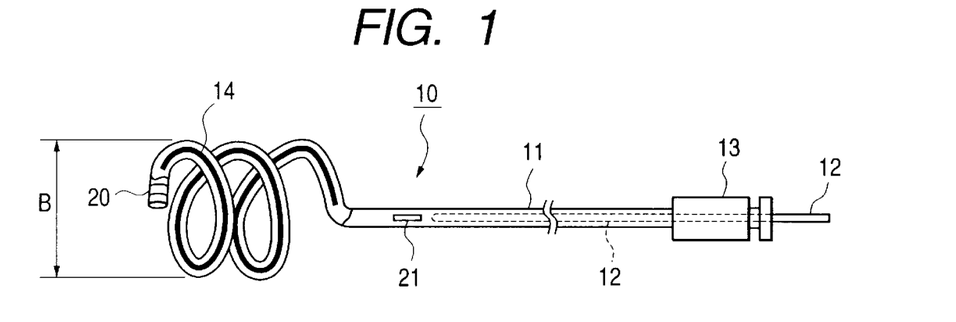
FIG. 1 is a partial cutaway side view to show an embodiment of the self-retaining catheter according to the present invention.

FIG. 1 illustrates an embodiment of the self-retaining catheter according to the present invention.

This self-retaining catheter 10 has a tubular catheter body 11, for example, made of a synthetic resin such as urethane, nylon, polyethylene, polypropylene, or silicone, or a shape memory alloy, or the like. A closure 13, which permits a core wire 12 to be inserted in a sealed state into the catheter body 11, is mounted at the base end of the catheter body 11. The core wire 12 can be selected from wires of shape memory alloys, stainless steel, or the like, guide wires, and so on.

The inside and/or the outside of the catheter body is preferably coated with a hydrophilic resin in order to enhance a sliding property of the core wire 12 to the catheter body 11 or in order to increase a sliding property of the catheter body 11 to a master catheter described hereinafter.

A coil wire 14 having higher stiffness than the catheter body 11 is buried inside the leading end of the catheter body 11. The wire 14 is made of a shape memory alloy treated by such a shape memory treatment as to exhibit superelasticity near body temperatures of the human body in the case of this embodiment, but the wire 14 may also be selected from wires of other metals such as stainless steel, wires of FRP with high stiffness, and so on. An outside diameter of the coil wire 14 in a free state is a diameter sufficiently larger than an inside diameter A of a self-retaining portion such as an objective blood vessel (see FIG. 11A). In the state in which the coil wire 14 is interpolated in the catheter body 11, the catheter body 11 is also in a winding shape like a coil having an outside diameter B larger than the inside diameter A of the self-retaining portion. Since the wire 14 has superelasticity while the catheter body 11 is made of a plastic pipe, they can be elastically deformed, so that they can be put inside an inside diameter C of the master catheter 51 (see FIG. 11A). In this state they can be inserted into a blood vessel or the like. A ring contrast chip 20 is mounted at the leading end of the catheter body 11.

Figure 2:
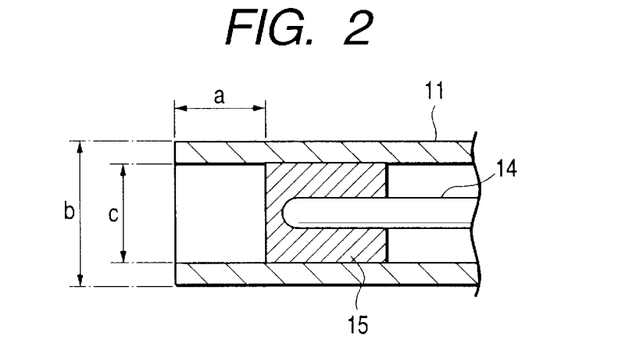
FIG. 2 is a partial sectional view to show a fixing structure of the wire at the leading end of the self-retaining catheter.

As shown in FIG. 2, the leading end of the wire 14 is fixed inside the catheter body 11 with an adhesive 15. This prevents the wire 14 from moving inside the catheter body 11. A distance a between the tip of the fixing part of wire 14 and the tip of the catheter body 11 is preferably 5–50 mm and most preferably about 20 mm. This range provides the leading end of the catheter body 11 with flexibility and thus prevents the leading end from damaging the inner wall of the blood vessel or the like. The size of the catheter body 11 may be properly determined depending upon an applied object, but, for example in the case of those for liver arteries of adults, the outside diameter b is preferably 0.3–2 mm and the inside diameter c is preferably 0.1–1.7 mm.

Figure 3A:
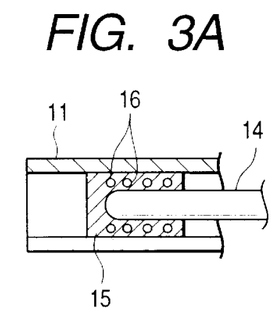
FIG. 3A, FIG. 3B, and FIG. 3C are partial sectional views to show other examples of the fixing structure of the wire.
Figure 3B:
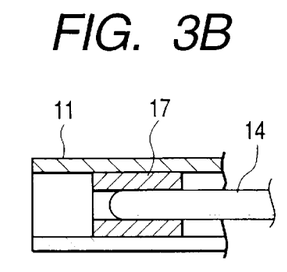
Figure 3C:
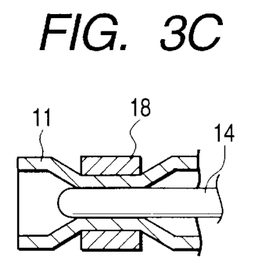

FIGS. 3A to 3C show other examples of the fixing structure of the leading end of wire 14.

In the example of FIG. 3A, a coil 16 is disposed around the periphery of the leading end of the wire 14, and the adhesive 15 is deposited so as to bury the coil 16 and the leading end of the wire 14, whereby the leading end of the wire 14 is fixed to the catheter body 11. In this example the coil 16 makes it easier to deposit the adhesive 15 and reduces the clearance between the wire 14 and the inner wall of the catheter body 11, so as to enhance the fixing strength.

In the example of FIG. 3B, a contrast chip 17 having a ring shape or a C-shaped cross section is put inside the catheter body 11, the leading end of the wire 14 is put in this contrast chip 17, and the leading end of the wire 14 is fixed by caulking of the contrast chip 17.

In the example of FIG. 3C, a contrast chip 18 having a ring shape or a C-shaped cross section is mounted on the periphery of the leading end of the catheter body 11, and the leading end of the wire 14 is fastened through the catheter body 11 by caulking of this contrast chip 18.

Figure 4:
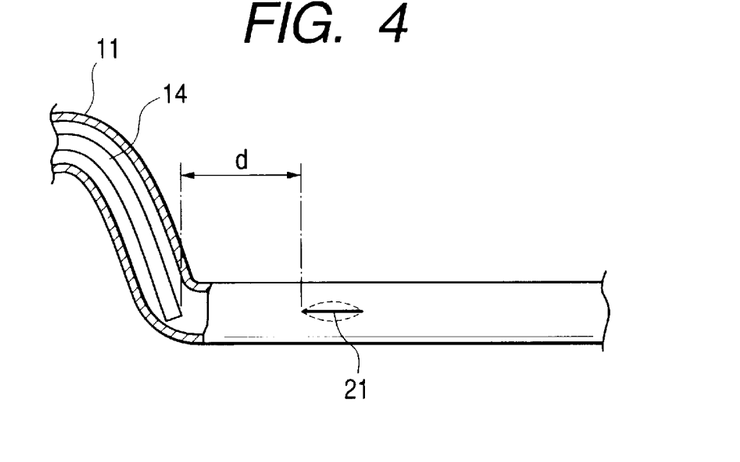
FIG. 4 is a partial sectional view to show the vicinity of an aperture through which a medical fluid in the self-retaining catheter flows out.

As shown in FIG. 1 and FIG. 4, an aperture 21 of a slit shape is formed in a peripheral wall a distance d apart from the base end of the wire 14 in the catheter body 11 to the base of the catheter body 11. The length of d is suitably set depending upon an applied portion, but it is normally 1–15 cm. When a pressure of a fluid is applied inside, the aperture 21 is opened as shown by the dotted line in FIG. 4. When the pressure of the fluid is not applied inside, the aperture 21 is closed. By this structure, the aperture is opened on the occasion of injection of a medical fluid, and during the other periods the body fluid such as the blood is prevented from flowing through the aperture 21 into the catheter body 11.

In an alternative way, the self-retaining catheters may be supplied in a selling form without the aperture 21, and the aperture 21 of the slit shape may be formed depending upon patient's conditions, for example by urging the tip of a knife or the like against the peripheral wall of the catheter body 11 to cut it immediately before an operation. The aperture 21 can be suitably formed by such working as to cut the wall with a knife or an edged tool having a fine edge. If the aperture 21 were made, for example, by machining with a grinder or the like, a part of the wall would be lost, so as to form an aperture always open. Therefore, the valve effect (the effect that the aperture is opened only when the pressure of the fluid is applied inside) would not be achieved well.

FIGS. 5A to 5D show other examples of the aperture.

Figure 5A:
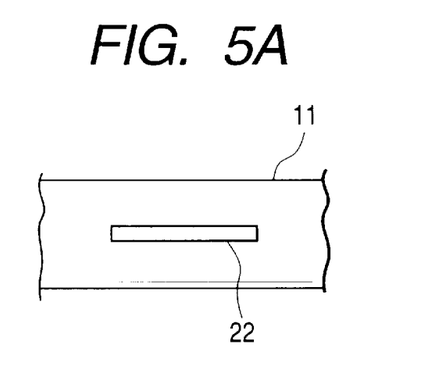
FIG. 5A, FIG. 5B, FIG. 5C, and FIG. 5D are explanatory drawings to show other examples of the shape of the aperture.
Figure 5B:
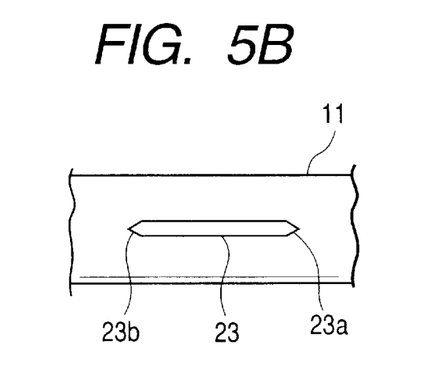
Figure 5C:
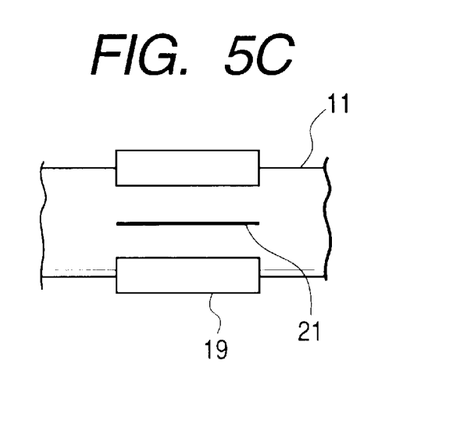
Figure 5D:
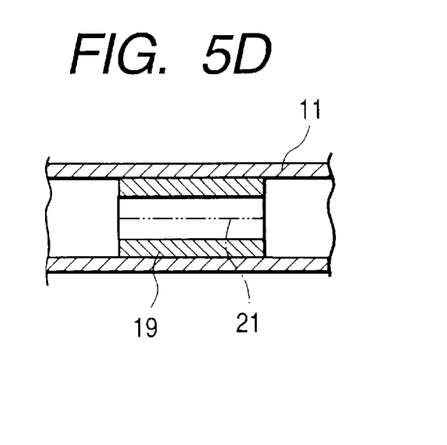

In the example of FIG. 5A an aperture 22 is formed in a predetermined width. In the example of FIG. 5B an aperture 23 is formed in a predetermined width and is tapered at the both ends 23a, 23b. In the example of FIG. 5C a contrast chip 19 having a C-shaped cross section is mounted so as not to cover the aperture 21, on the periphery of the portion of the catheter body 11 where the aperture 21 is present, whereby the contrast chip 19 prevents the catheter body 11 from being crushed in the portion of aperture 21. In the example of FIG. 5D a contrast chip 19 also having a C-shaped cross section is set so as not to close the aperture 21, on the inside surface of the portion where the aperture 21 is formed in the catheter body 11, whereby the contrast chip 19 prevents the catheter body 11 from being crushed in that portion.

Figure 6:
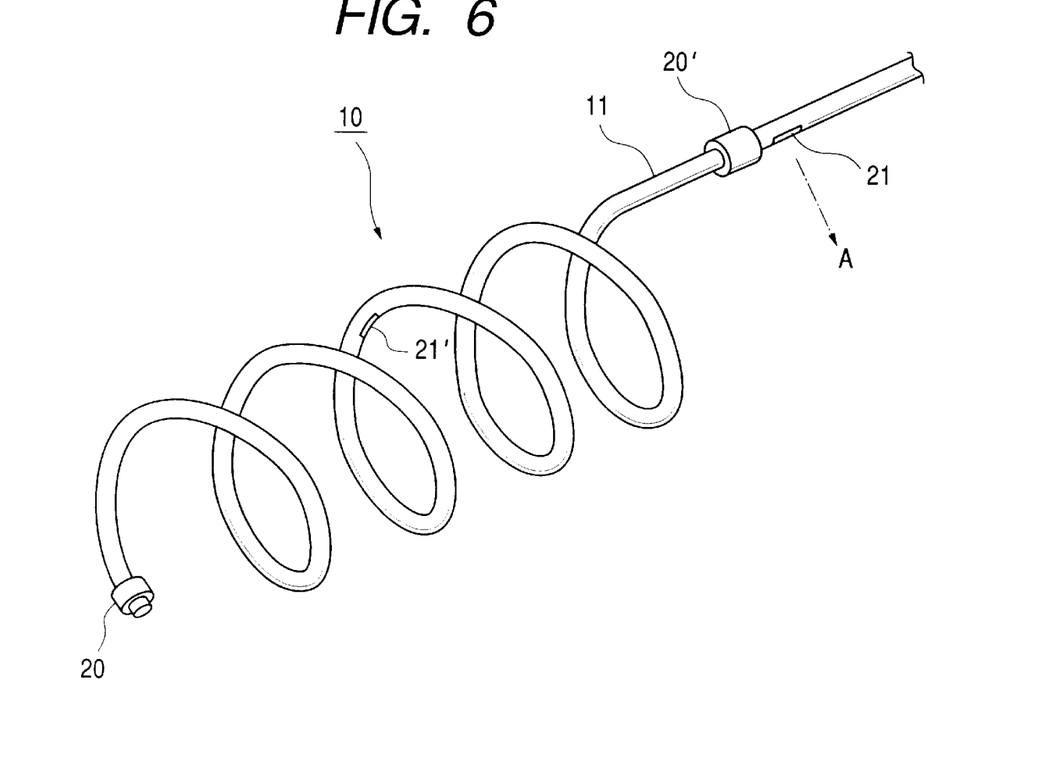
FIG. 6 is a perspective view to show the shape of the leading end of the self-retaining catheter.

FIG. 6 is a perspective view to show an enlarged view of the leading end of the self-retaining catheter 10.

The leading end of the self-retaining catheter 10 is kept in the winding state of the coil shape by the wire 14 (not illustrated in FIG. 6) disposed inside the catheter body 11 as long as no external force is exerted thereon. The base side of the catheter body 11 linearly extends from a position in a periphery of this coil winding portion. Because of this shape, when the self-retaining catheter is set in a tubular organ such as a blood vessel, the base side of the catheter body 11 extends along the inner wall of the tubular organ and thus is arranged so as not to be positioned in the center of the lumen of the tubular organ.

The aperture 21 formed in the peripheral wall of the catheter body 11 is open while being directed in the direction A toward the center of the coil winding portion. This allows the aperture 21 to be directed inwardly of the tubular organ when the catheter is inserted into the tubular organ such as the blood vessel. This structure is free of the problem that when the medical fluid is allowed to flow through the aperture 21, the medical fluid is ejected strongly against the intima of the tubular organ to be directly absorbed through the intima, or the aperture is pushed against the intima of the tubular organ to interfere ejection of the medical fluid.

While the contrast chip 20 is provided at the leading end of the catheter body 11, another contrast chip 20' may also be mounted near the aperture 21 in place of this contrast chip 20 or together with the contrast chip 20. This allows the position of the aperture through which the medical fluid is ejected, to be detected more accurately. These contrast chips 20, 20' may also be located in the catheter body 11.

The aperture 21' may be formed on the inside of the winding portion of the spiral shape, instead of the aperture 21 formed in the straight portion of the catheter body 11. In this case the medical fluid is introduced through the clearance between the internal surface of the catheter body 11 and the wire 14 to the spirally winding portion of the catheter body 11 to flow out through the aperture 21'.

Figure 7:
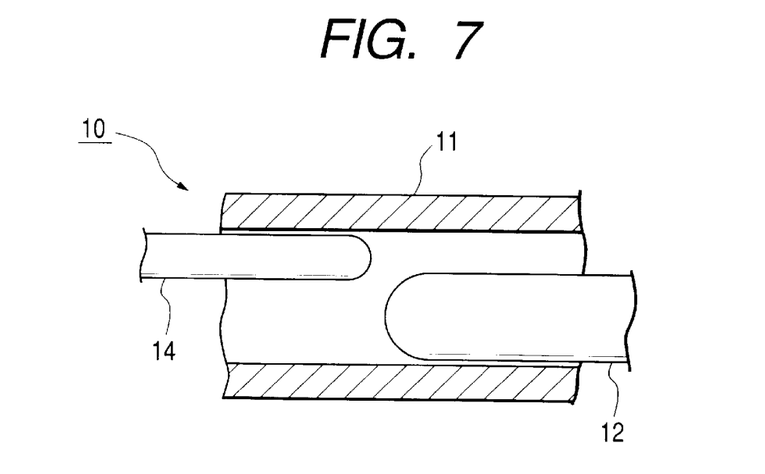
FIG. 7 is a partial sectional view to show the relation between the wire and the core wire of the self-retaining catheter.

FIG. 7 illustrates the relation between the wire 14 and the core wire 12 in the self-retaining catheter 10. As illustrated, the base end of the wire 14 extends toward the base of the catheter body 11, and the leading end of the core wire 12 extends toward the tip of the catheter body 11 and has such a thickness as to abut against the base end of the wire 14. This structure allows a pushing force to be occur in the self-retaining catheter 10 when the core wire 12 is forced into the catheter body 11.

Figure 8:
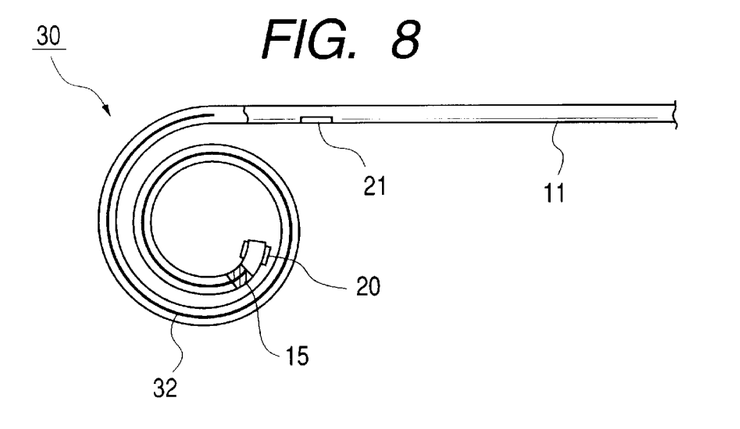
FIG. 8 is a partial sectional view to show another embodiment of the self-retaining catheter according to the present invention.

FIG. 8 illustrates another embodiment of the self-retaining catheter according to the present invention. Substantially identical portions to those in the embodiment shown in FIG. 1 will be denoted by the same reference numerals and the description thereof will be omitted herein.

In the self-retaining catheter 30 of this embodiment a swirl of wire 32 is put inside the leading end of the catheter body 11 and the leading end of the wire 32 is fixed to the catheter body 11 with the adhesive 15. As a result, the catheter body 11 is kept in a swirl shape by the stiffness of the wire 32 as long as no external force is exerted thereon. In the case of this embodiment the base side of the catheter body 11 also linearly extends from the periphery of the swirl winding portion and the aperture 20 is open as directed toward the center of the winding portion. As described above, a variety of shapes can be employed for the winding shape of the wire.

Figures 9, 10:
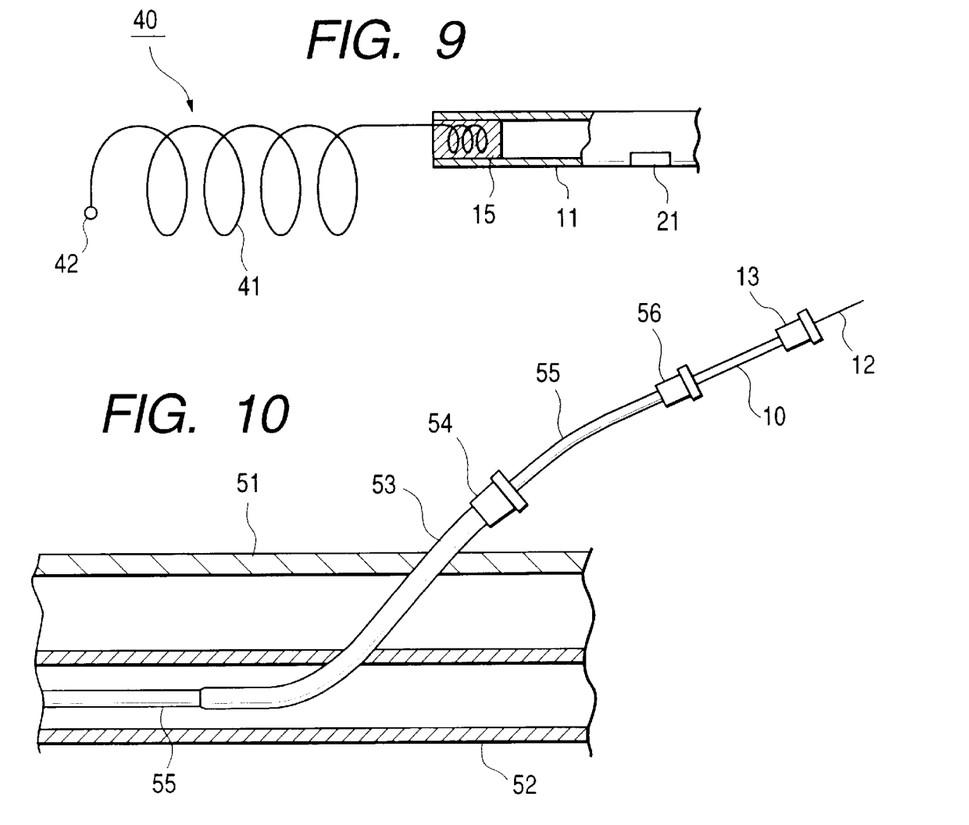
FIG. 9 is a partial sectional view to show still another embodiment of the self-retaining catheter according to the present invention.
FIG. 10 is an explanatory drawing to show a state in which the self-retaining catheter is being percutaneously inserted into a blood vessel.

FIG. 9 illustrates still another embodiment of the self-retaining catheter according to the present invention.

In the self-retaining catheter 40 of this embodiment one end of wire 41 of a coil shape is connected to the leading end of the catheter body 11 and the wire 41 projects out of the catheter body 11. The diameter of the coil of wire 41 is larger than the outside diameter of the catheter body 11 and a contrast chip 42 is formed at the tip of the wire 41 by melting the wire in a ball shape or by welding a metal not transmitting X-rays, such as platinum or a platinum alloy, to the tip. This contrast chip 42 also presents the effect of preventing the inner wall of the tubular organ from being damaged. The outside surface of the wire 41 is preferably coated with an organism-compatible resin.

The base end of the wire 41 is formed in a small coil shape, put in the catheter body 11, and fixed thereto with the adhesive 15. In the case of this embodiment the base side of the catheter body 11 also linearly extends from the periphery of the wire 41 of the coil shape and the aperture 21 formed in the peripheral wall of the catheter body 11 is open as being directed to the center of the coil shape of the wire 41. As in this embodiment, the wire as a fixing means to the tubular organ may project outwardly from the catheter body 11.

Next, a method for administering a carcinostatic to liver arteries by use of the self-retaining catheter 10 shown in FIG. 1 will be described referring to FIG. 10 to FIG. 15.

Figure 12:
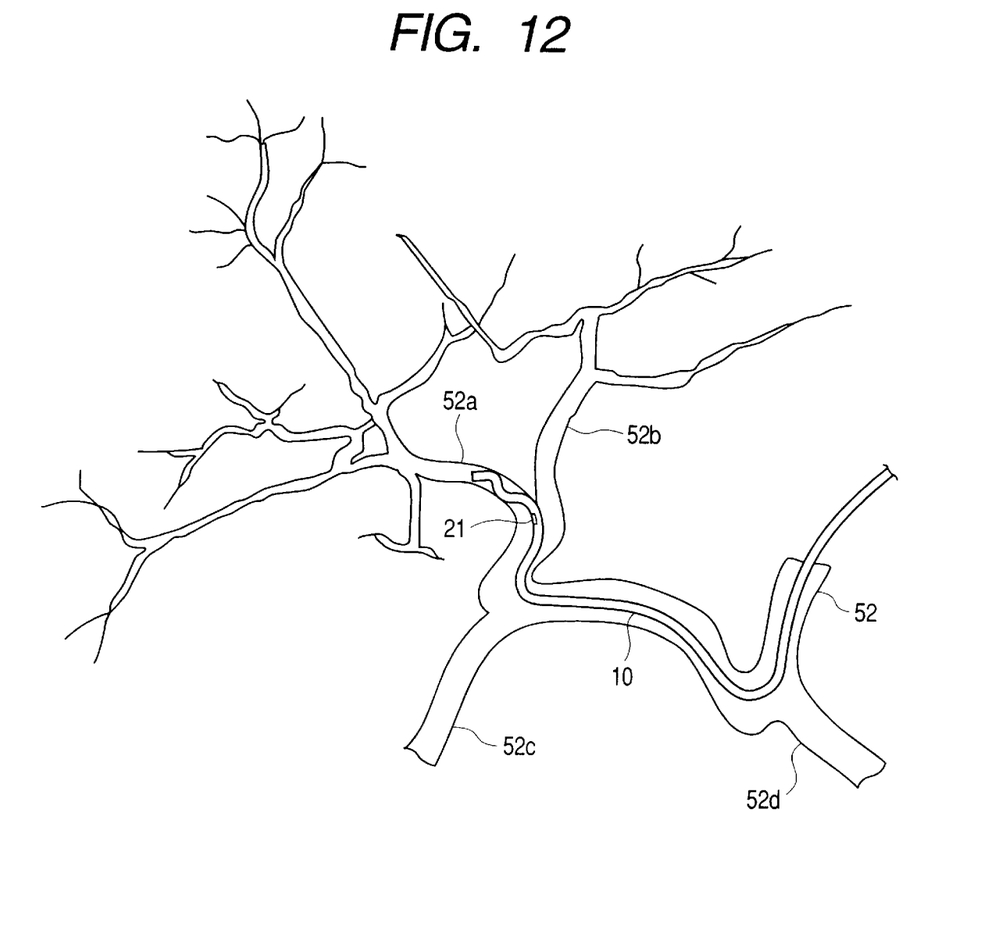
FIG. 12 is an explanatory drawing to show a state in which the leading end of the self-retaining catheter is fixed at a target portion of a blood vessel.
Figure 13:
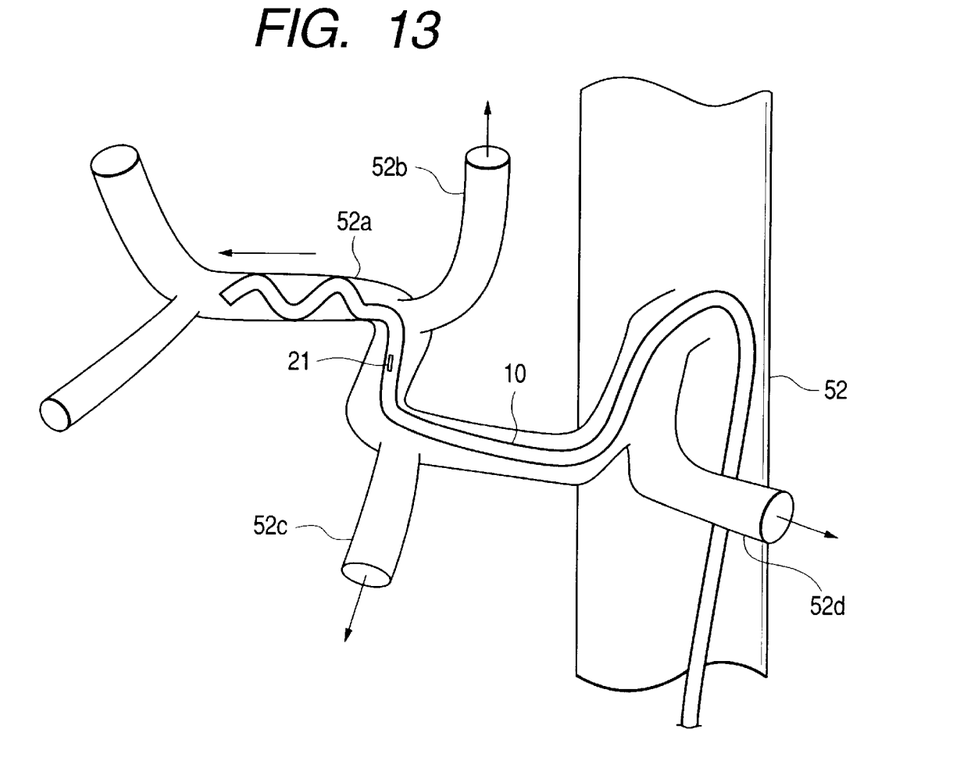
FIG. 13 is an explanatory drawing to schematically show an enlarged state in which the leading end of the self-retaining catheter is fixed at the target portion of the blood vessel.
Figure 14:
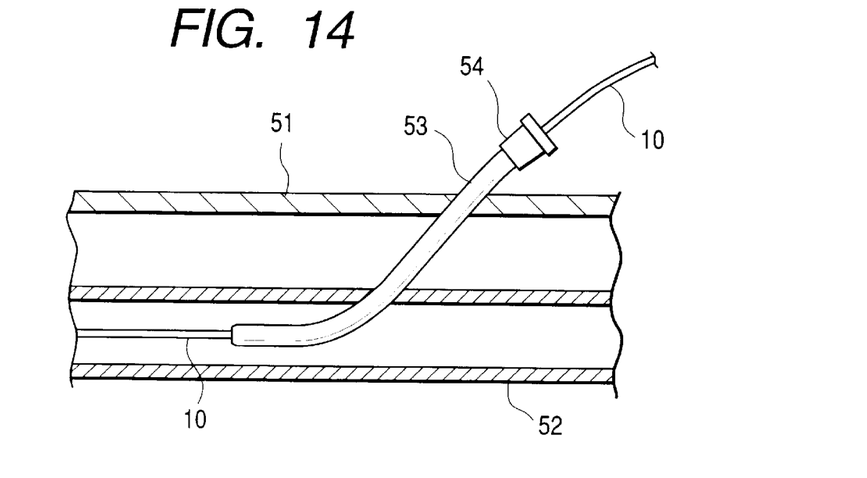
FIG. 14 is an explanatory drawing to show a state in which the master catheter is retracted.
Figure 15:
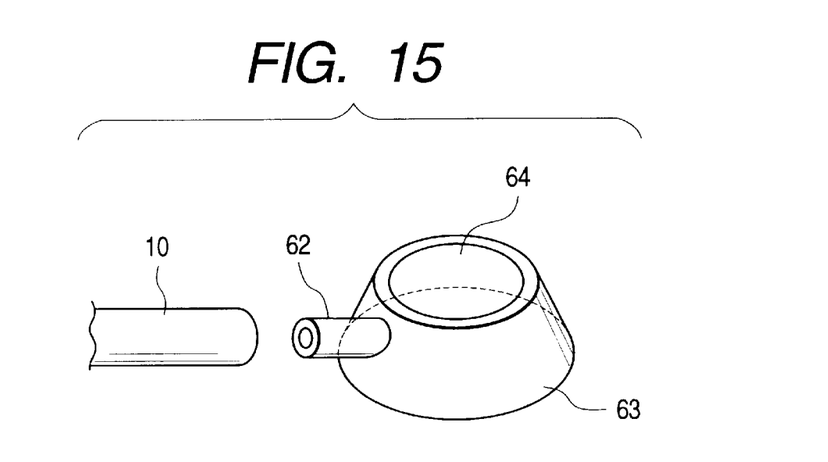
FIG. 15 is a perspective view to show a medical fluid injection port.
Figure 16:
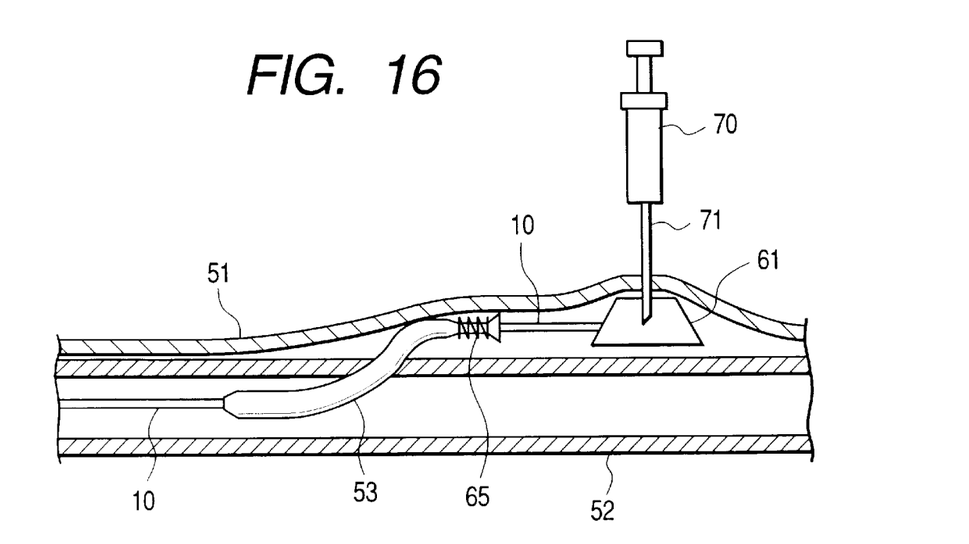
FIG. 16 is an explanatory drawing to show a state in which the medical fluid injection port is embedded under the skin and in which the medical fluid is supplied thereto with an injection syringe.

FIG. 10 is an explanatory drawing to show a state in which the self-retaining catheter 10 is percutaneously inserted into a blood vessel; FIGS. 11A to 11E are explanatory drawings to show procedures for inserting the self-retaining catheter 10 through the master catheter into the blood vessel and allowing the medical fluid to flow out; FIG. 12 is an explanatory drawing to show a state in which the leading end of the self-retaining catheter 10 is set at an objective portion of a blood vessel and fixed there; FIG. 13 is an explanatory drawing to schematically show an enlarged state in which the leading end of the self-retaining catheter 10 is set at the objective portion of the blood vessel and fixed there; FIG. 14 is an explanatory drawing to show a state in which the master catheter is withdrawn; FIG. 15 is a perspective view to show a medical fluid injection port; FIG. 16 is an explanatory drawing to show a state in which the medical fluid injection port is buried under the skin and in which the medical fluid is supplied thereto with an injection syringe.

In FIG. 10, numeral 51 designates the skin and 52 a blood vessel (the femoral artery in this example). First, a sheath 53 is percutaneously inserted into the blood vessel 52 by the known Seldinger method. Then the master catheter 55 is inserted through a closure 54 provided at the base end of the sheath 53. Further, a guide wire not illustrated is inserted through a closure 56 provided at the base end of the master catheter 55. After the leading end of the guide wire reaches an objective portion of a blood vessel, the leading end of the master catheter 55 is forced ahead along the guide wire up to the aforementioned portion, and then the guide wire is pulled out.

Then the self-retaining catheter 10 is inserted through the closure 56 provided at the base end of the master catheter 55 and the core wire 12 is inserted through the closure 13 provided at the base end of the self-retaining catheter 10. Then the self-retaining catheter 10 is forced into the master catheter 55 while the stiffness is maintained by the core wire 12. For example, supposing the size of the sheath 53 is 5 Fr (French size), the size of the master catheter 55 is 4 Fr.

Figure 11A:
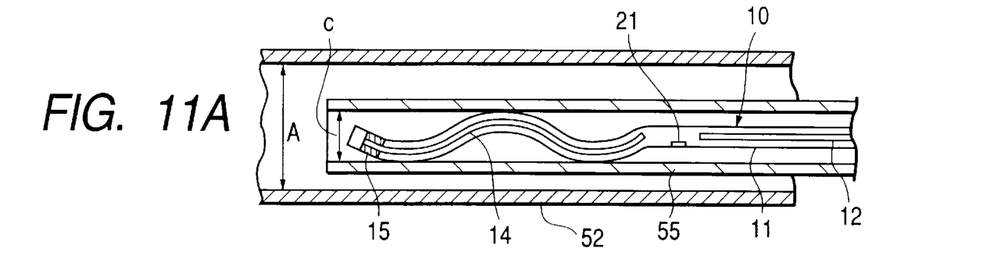
FIG. 11A, FIG. 11B, FIG. 11C, FIG. 11D, and FIG. 11E are explanatory drawings to show procedures for inserting the self-retaining catheter into the blood vessel through the master catheter and allowing the medical fluid to flow out therethrough.

As shown in FIG. 11A, the leading end of the self-retaining catheter 10 inserted into the master catheter 55 passes in the master catheter 55 while the coil wire 14 inside the catheter body 11 is stretched in a wave shape.

Figure 11B:
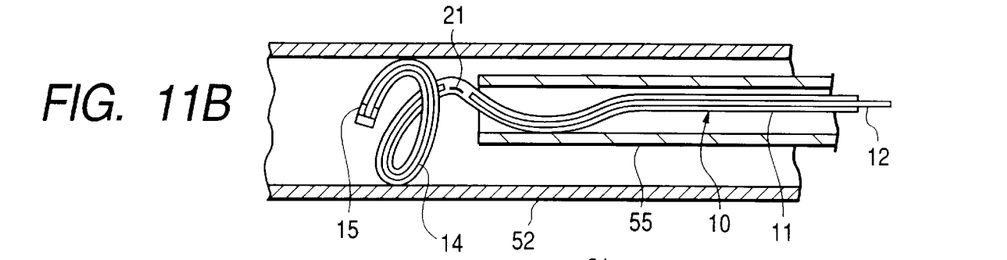

When the master catheter 55 is pulled to project the leading end of the self-retaining catheter 10 out as shown in FIG. 11B, the leading end of the self-retaining catheter 10 elastically returns to the original coil diameter in the free state from the depressed state where it is limited to the inside diameter of the master catheter 55. Then the leading end of the self-retaining catheter 10 is elastically urged against the inner wall of the blood vessel 52.

Figure 11C:
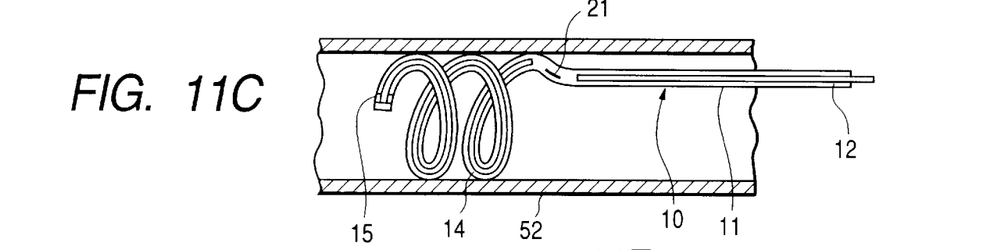
Figure 11D:
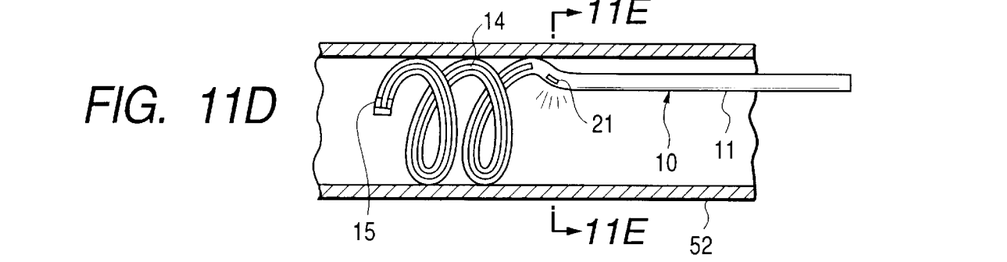
Figure 11E:
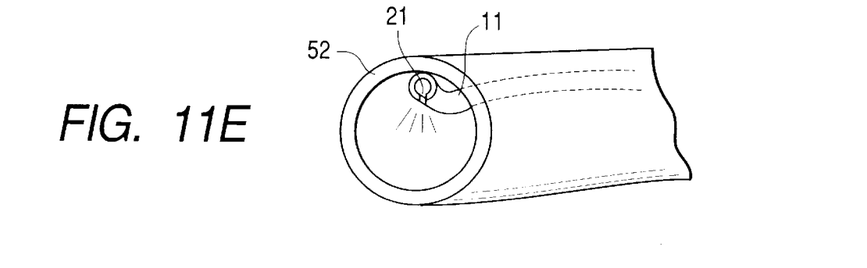

FIG. 11C shows a state in which the master catheter 55 is drawn out by the above operation and FIG. 11D shows a state in which the core wire 12 is pulled out and the medical fluid is injected into the self-retaining catheter 10 to flow out through the aperture 21. FIG. 11E is a sectional view along line e—e in FIG. 11D, which shows a state in which the medical fluid is flowing out toward the center of the blood vessel 52.

In FIG. 12 and FIG. 13, 52a designates the right liver artery to which the carcinostatic is expected to be administered, 52b the left liver artery, 52c the gastroduodenal artery, and 52d the splenic artery. It can also be contemplated that, prior to the administration of the carcinostatic, the embolization coils or the like are preliminarily inserted into blood vessels branched to normal organs to temporarily embolize those blood vessels so as to prevent the medical fluid containing the carcinostatic from flowing into the normal organs. In the case wherein the treatment continues over the long period while the self-retaining catheter 10 is buried in the body, it is, however, preferred to avoid the above embolization operation with the embolization coils while the aperture 21 of the self-retaining catheter 10 is positioned as close to the affected part as possible.

The leading end of the self-retaining catheter 10 is set, for example, in the right liver artery 52a to be fixed as being expanded by the restoring force of the wire 14 and being urged against the inner wall of the blood vessel in that portion. At this time the aperture 21 of the self-retaining catheter 10 is located at a branch point into the right liver artery 52a and the left liver artery 52b so that the medical fluid flowing through the aperture 21 can flow mainly in directions to the entire liver. Since the leading end of the self-retaining catheter 10 is fixed in the blood vessel, there is no possibility of a positional shift of the aperture 21 even if the patient turns his body thereafter.

After the leading end of the self-retaining catheter 10 is set at the objective portion as described above, the core wire 12 is withdrawn and the master catheter 55 is further withdrawn, thereby establishing the state in which only the self-retaining catheter 10 is put in the sheath 53, as shown in FIG. 14. In this state the closure 54 of the sheath 53 and the closure 13 side of the self-retaining catheter 10 are disconnected, so as to project the self-retaining catheter 10 out from the base portion of the sheath 53.

As shown in FIG. 15, the base portion of the self-retaining catheter 10 thus cut is connected to a medical fluid outlet 62 of a medical fluid injection port 61. The medical fluid injection port 61 is constructed in such a structure that a container 63 having a truncated cone shape is made of a synthetic resin having a hardness too high for the injection needle or the like to pierce, a rubber film 64, through which the injection needle or the like can be stuck, is mounted in an aperture of the top surface of the container 63, and the aforementioned medical fluid outlet 62 is formed in the side wall of the container 63.

As shown in FIG. 16, after the skin 51 is incised, the medical fluid injection port 61 is buried inside the skin 51. At this time the base portion of the sheath 53 cut is fastened to the self-retaining catheter 10 with thread 65 or the like, thereby preventing the blood from leaking from that portion. In this state the patient can live the daily life as being allowed to move freely. During that period, the catheter will not shift in the body, because the leading end of the self-retaining catheter 10 is fixed as shown in FIG. 12 and FIG. 13.

For periodically administering the carcinostatic, the injection needle 71 of the injection syringe 70 is stuck through the skin 51 into the rubber film 64 of the medical fluid injection port 61 and the medical fluid in which the carcinostatic is dissolved is injected into the medical fluid injection port 61. This medical fluid flows out of the medical fluid outlet 62 into the self-retaining catheter 10 and flows out through the aperture 21 of the self-retaining catheter 10. Then the medical fluid can be selectively injected into the liver affected by cancer. The medical fluid advances along the axis of the catheter in the self-retaining catheter 10 and then turns the direction to flow out sideways through the aperture 21 provided in the peripheral wall of the self-retaining catheter 10. Therefore, the medical fluid is prevented from strongly hitting the inner wall of the blood vessel, and there is thus little damage to the inner wall of the blood vessel.

It is also contemplated that a plurality of fine self-retaining catheters of about 1.5 Fr are simultaneously set through one blood vessel and are retained at different portions inside the human body. In this case, only medical fluids necessary for a plurality of organs can be simultaneously injected and administered to the respective organs; for example, a medical fluid A is administered to the liver arteries, a medical fluid B to the gastroduodenal artery, and a medical fluid C to the splenic artery. This can remarkably enhance the treatment effects on a patient suffering combined diseases and can decrease the treatment period.

What is claimed is:

1. A self-retaining catheter comprising:
   a tubular catheter body; and
   a wire having an elastic portion which is formed resiliently into a winding shape, said wire being connected to a leading end portion of the catheter body, wherein said self-retaining catheter is able to be self-retained by acting resilient force, which is raised by the resilient deformation of said elastic portion, on an inner wall of a tubular organ, said self-retaining catheter including;

an aperture for outflow of a medical fluid, said aperture being formed in a slit shape, said aperture opening when a pressure of the fluid inside said catheter is applied thereto, said aperture closing when the pressure of the fluid in said catheter is not applied thereto, said aperture being arranged so as not to overlap with said wire; and a contrast chip mounted near said aperture.

2. A self-retaining catheter according to claim 1, wherein said wire is buried in the leading end portion of said catheter body.

3. A self-retaining catheter according to claim 1, wherein said wire is connected to one end of said catheter body so as to project outwardly from said catheter body.

4. A self-retaining catheter according to claim 1, wherein said catheter body linearly extends from a position in a periphery of said winding shape to a proximal (or base) end of said catheter body.

5. The self-retaining catheter according to claim 1, further comprising an aperture for outflow of a medical fluid, said aperture being formed in a peripheral wall of said catheter body near the end thereof where said wire is mounted, said aperture being formed in a slit shape, said aperture opening when a pressure of the fluid inside said catheter is applied thereto, and said aperture closing when the pressure of the fluid inside said catheter is not applied thereto.

6. The self-retaining catheter according to claim 1, wherein said aperture is formed as being directed toward the center of the winding shape of said wire.

7. The self-retaining catheter according to claim 5, wherein a contrast chip is mounted near said aperture of said catheter body.

8. A self-retaining catheter inserting apparatus comprising the self-retaining catheter according to claim 1, a core wire arranged to be detachably inserted into the self-retaining catheter, and a master catheter having an inside diameter that permits insertion of said self-retaining catheter.

9. A self-retaining catheter inserting apparatus comprising the self-retaining catheter according to claim 1, a core wire arranged to be detachably inserted into the self-retaining catheter, a master catheter having an inside diameter that permits insertion of said self-retaining catheter, and a sheath for percutaneous insertion of said master catheter into a tubular organ.

10. A self-retaining catheter inserting apparatus comprising the self-retaining catheter according to claim 1, a core wire arranged to be detachably inserted into the self-retaining catheter, a master catheter having an inside diameter that permits insertion of said self-retaining catheter, a sheath for percutaneous insertion of said master catheter into a blood vessel, and a medical fluid injection port to be embedded in the body while being connected to a base end of the self-retaining catheter.

11. A self-retaining catheter according to claim 1, wherein said wire is buried in the leading end portion of said catheter body, and a given space between a leading end of said wire and the leading end of said catheter body is provided.

12. A self-retaining catheter according to claim 1, wherein said contrast chip has a C-shaped cross section and an opening portion of said C-shape is mounted so as to be coincided with a longitudinal direction of said slit shape while surrounding said slit shape.

13. A self-retaining catheter comprising:

a tubular catheter body; and a wire having an elastic portion which is formed resiliently into a winding shape, said wire being connected to a leading end portion of the catheter body, wherein said self-retaining catheter is able to be self-retained by acting resilient force, which is raised by the resilient deformation of said elastic portion, on an inner wall of a tubular organ, said self-retaining catheter being characterized by including an aperture for outflow of a medical fluid, said aperture being formed in a slit shape, said aperture opening when a pressure of the fluid inside said catheter is applied thereto, and said aperture closing when the pressure of the fluid in said catheter is not applied thereto, and in that said wire is buried in the lead end portion of said catheter body, and a given space between a leading end of said wire and the leading end of said catheter body is provided.

14. A self-retaining catheter comprising:

a tubular catheter body; and a wire having an elastic portion which is formed resiliently into a winding shape, said wire being connected to a leading end portion of the catheter body, wherein said self-retaining catheter is able to be self-retained by acting resilient force, which is raised by the resilient deformation of said elastic portion, on an inner wall of a tubular organ, said self-retaining catheter being characterized by including;

an aperture for outflow of a medical fluid, said aperture being formed In a slit shape, said aperture opening when a pressure of the fluid inside said catheter is applied thereto, said aperture closing when the pressure of the fluid in said catheter is not applied thereto; and a contrast chip being mounted near said aperture, and in that said aperture is arranged so as not to overlap with said wire and said contrast chip has a C-shaped cross section and an opening portion of said C-shape is mounted so as to be coincided with a longitudinal direction of said slit shape while surrounding said slit shape.

* * * * *